US00PP32476P2

(12) United States Plant Patent
Blom

(10) Patent No.: US PP32,476 P2
(45) Date of Patent: Nov. 17, 2020

(54) ***CHRYSANTHEMUM* PLANT NAMED 'ZANMUMAMIA'**

(50) Latin Name: ***Chrysanthemum* X *morifolium***
Varietal Denomination: Zanmumamia

(71) Applicant: Wilhelmus Bernardus Blom, Leimuiden (NL)

(72) Inventor: Wilhelmus Bernardus Blom, Leimuiden (NL)

(73) Assignee: VAN ZANTEN BREEDING B.V., Rijsenhout (NL)

( * ) Notice: Subject to any disclaimer, the term of this patent is extended or adjusted under 35 U.S.C. 154(b) by 0 days.

(21) Appl. No.: 16/873,144

(22) Filed: Feb. 12, 2020

(51) Int. Cl.
*A01H 5/02* (2018.01)
*A01H 6/14* (2018.01)

(52) U.S. Cl.
USPC ..... Plt./293
CPC ..... *A01H 6/1424* (2018.05)

(58) Field of Classification Search
USPC ..... Plt./293
CPC ..... A01H 6/1424; A01H 5/02
See application file for complete search history.

*Primary Examiner* — Keith O. Robinson
(74) *Attorney, Agent, or Firm* — C. A. Whealy

(57) ABSTRACT

A new and distinct cultivar of *Chrysanthemum* plant named 'Zanmumamia', characterized by its upright, outwardly spreading and uniformly spherical plant habit; vigorous growth habit; freely branching habit; dense and full plant habit; dark green-colored leaves; uniform and freely flowering habit; long flowering period; decorative-type inflorescences with ray florets that are dark red in color; and good garden performance.

1 Drawing Sheet

Botanical designation: *Chrysanthemum* X *morifolium*.
Cultivar denomination: 'ZANMUMAMIA'.

BACKGROUND OF THE INVENTION

The present invention relates to a new and distinct cultivar of *Chrysanthemum* plant, botanically known as *Chrysanthemum* X *morifolium*, commercially referred to as a Garden Mum and hereinafter referred to by the name 'Zanmumamia'.

The new *Chrysanthemum* plant is a product of a planned breeding program conducted by the Inventor in Rijsenhout, The Netherlands. The objective of the breeding program is to create new uniform spherically-shaped and freely flowering *Chrysanthemum* plants with unique and attractive ray floret coloration.

The new *Chrysanthemum* plant originated from a cross-pollination in November, 2011 of a proprietary selection of *Chrysanthemum* x *morifolium* identified as code number 10-010457, not patented, as the female, or seed, parent with a proprietary selection of *Chrysanthemum* x *morifolium* identified as code number 38.9526, not patented, as the male, or pollen, parent. The new *Chrysanthemum* plant was discovered and selected as a single flowering plant from within the progeny of the stated cross-pollination in a controlled greenhouse environment in Rijsenhout, The Netherlands in July, 2012.

Asexual reproduction of the new *Chrysanthemum* plant by vegetative terminal cuttings was first conducted in a controlled greenhouse environment in Rijsenhout, The Netherlands in September, 2012. Asexual reproduction by vegetative terminal cuttings has shown that the unique features of this new *Chrysanthemum* plant are stable and reproduced true to type in successive generations.

SUMMARY OF THE INVENTION

The following traits have been repeatedly observed and are determined to be the unique characteristics of 'Zanmumamia'. These characteristics in combination distinguish 'Zanmumamia' as a new and distinct *Chrysanthemum* plant:

1. Upright, outwardly spreading and uniformly spherical plant habit; vigorous growth habit.
2. Freely branching habit; dense and full plant habit.
3. Dark green-colored leaves.
4. Uniform and freely flowering habit.
5. Long flowering period.
6. Decorative-type inflorescences with ray florets that are dark red in color.
7. Good garden performance.

Plants of the new *Chrysanthemum* can be compared to plants of the female selection parent. Plants of the new *Chrysanthemum* differ primarily from plants of the female parent selection in ray floret color as ray florets of plants of the new *Chrysanthemum* are brighter red than and not as dull red as ray florets of plants of the female parent selection.

Plants of the new *Chrysanthemum* can be compared to plants of the male selection parent. Plants of the new *Chrysanthemum* differ primarily from plants of the male parent selection in plant form as plants of the new *Chrysanthemum* are spherical in form whereas plants of the male parent selection are upright in form. In addition, plants of the new *Chrysanthemum* have larger inflorescences than plants of the male parent selection.

Plants of the new *Chrysanthemum* can also be compared to plants of *Chrysanthemum* X *morifolium* 'Zanmurover', disclosed in U.S. Plant Pat. No. 23,016. In side-by-side comparisons, plants of the new *Chrysanthemum* differ primarily from plants of 'Zanmurover' in the following characteristics:

1. Under natural season conditions, plants of the new *Chrysanthemum* flower about one to two weeks earlier than plants of 'Zanmurover'.

2. Inflorescences of plants of the new *Chrysanthemum* have fewer ray florets than inflorescences of plants of 'Zanmurover'.

BRIEF DESCRIPTION OF THE PHOTOGRAPH

The accompanying photograph illustrates the overall appearance of the new *Chrysanthemum* plant showing the colors as true as it is reasonably possible to obtain in colored reproductions of this type. The photograph (FIG. 1) comprises a side perspective view of a typical flowering plant of 'Zanmumamia' grown in a container.

DETAILED BOTANICAL DESCRIPTION

The aforementioned photograph and following observations and measurements describe plants grown in 17-cm containers in an outdoor nursery in Rijsenhout, The Netherlands under natural daylengths during the summer and autumn and under cultural practices generally used in commercial *Chrysanthemum* production. During the production of the plants, day temperatures ranged from 15° C. to 25° C. and night temperatures ranged from 8° C. to 15° C. Plants were 19 weeks from planting when the photograph was taken and the detailed description was taken on plants from 14 to 20 weeks after planting. In the following description, color references are made to The Royal Horticultural Society Colour Chart, 2015 Edition, except where general terms of ordinary dictionary significance are used.

Botanical classification: *Chrysanthemum* X *morifolium* 'Zanmumamia'.

Parentage:

*Female, or seed, parent*.—Proprietary selection of *Chrysanthemum* X *morifolium* identified as code number 10-010457, not patented.

*Male, or pollen, parent*.—Proprietary selection of *Chrysanthemum* X *morifolium* identified as code number 38.9526, not patented.

Propagation:

*Type cutting*.—By vegetative tip cuttings.

*Time to initiate roots, summer*.—About six to eight days at temperatures about 12° C. to 23° C.

*Time to produce a rooted young plant, summer*.—About 12 to 13 days at temperatures about 12° C. to 23° C.

*Root description*.—Thin, fibrous; typically close to 164D in color, actual color of the roots is dependent on substrate composition, water quality, fertilizer type and formulation, substrate temperature and physiological age of roots.

*Rooting habit*.—Freely branching; dense.

Plant description:

*Appearance*.—Perennial decorative-type *Chrysanthemum*; stems upright and outwardly spreading giving a uniformly rounded appearance to the plant; plants roughly spherical; very freely branching habit, about nine to ten primary lateral branches develop, each primary lateral branch with about nine to ten secondary branches; dense and full plant habit; vigorous growth habit; rapid growth rate.

*Plant height*.—About 35 cm.

*Plant width*.—About 50 cm.

*Lateral branches*.—Length: About 10 cm to 16 cm. Diameter: About 2.5 mm. Internode length: About 4 mm to 25 mm. Strength: Moderately strong, flexible. Aspect: About 30° to 45° from vertical. Texture and luster: Pubescent, fine; longitudinally ridged; matte. Color: Close to 138B; with development, becoming closer to 199B.

*Leaves*.—Arrangement: Alternate, simple. Length: About 2 cm to 4 cm. Width: About 1.2 cm to 2.4 cm. Shape: Elliptic. Apex: Acute. Base: Attenuate. Margin: Palmately lobed, sinuses between lateral lobes divergent and medium in depth. Texture and luster, upper surface: Pubescent; slightly glossy. Texture and luster, lower surface: Smooth, glabrous; matte. Venation: Pinnate. Color: Developing leaves, upper surface: Close to 143B. Developing leaves, lower surface: Close to 138A. Fully expanded leaves, upper surface: Close to NN137A; venation, close to 147D. Fully expanded leaves, lower surface: Close to 138B; venation, close to 148D. Petioles: Length: About 4 mm to 10 mm. Diameter: About 1.5 mm to 2 mm. Strength: Moderately strong, flexible. Texture and luster, upper and lower surfaces: Smooth, glabrous; semi-glossy. Color, upper surface: Close to 147D. Color, lower surface: Close to 148D.

Inflorescence description:

*Appearance*.—Decorative-type inflorescence form; inflorescences borne on terminals above foliar plane; ray florets arranged acropetally on a capitulum; inflorescences facing upright to outwardly.

*Fragrance*.—Slightly fragrant, pungent.

*Flowering response*.—Under natural season conditions, plants flower during October in The Netherlands.

*Postproduction longevity*.—Inflorescences maintain good color and substance for about three weeks in an outdoor nursery; inflorescences persistent.

*Quantity of inflorescences*.—About 1,000 inflorescences develop per plant.

*Inflorescence buds*.—Height: About 8 mm. Diameter: About 8 mm. Shape: Rounded. Texture and luster: Pubescent; semi-glossy. Color: Close to N138B.

*Inflorescence diameter*.—About 5 cm to 5.5 cm.

*Inflorescence depth* (*height*).—About 1.8 cm.

*Disc diameter*.—To date disc floret development has not been observed on plants of the new *Chrysanthemum*.

*Receptacle diameter*.—About 3 mm.

*Receptacle height*.—About 3 mm.

*Receptacle shape*.—Domed.

*Receptacle color*.—Close to 138C.

*Ray florets*.—Number of ray florets per inflorescence: About 120 to 130 arranged in about ten whorls. Length, developed: About 2.5 cm to 2.8 cm. Width, developed: About 5 mm to 6 mm. Shape, developed: Elliptic. Apex, developed: Emarginate. Base: Attenuate. Margin: Entire. Aspect: Mostly flat. Texture and luster, upper and lower surfaces: Smooth, glabrous; matte. Color: When opening, upper surface: Close to 187B. When opening, lower surface: Close to 183A. Fully opened, upper surface: Close to 183A; color becoming closer to 178B development. Fully opened, lower surface: Close to 185A; color becoming closer to 173A with development.

*Phyllaries*.—Number of phyllaries per inflorescence: About 21 to 24 arranged in about three whorls. Length: About 4 mm. Width: About 1.5 mm. Shape: Narrowly elliptic. Apex: Acute. Base: Attenuate. Margin: Entire. Texture and luster, upper and lower surfaces: Pubescent; semi-glossy. Color, upper surface: Close to 138D. Color, lower surface: Close to 138A.

*Peduncles*.—Length: About 6 cm. Diameter: About 1.5 mm. Angle: About 45° from stem axis. Strength: Strong. Texture and luster: Pubescent; matte. Color: Close to 138B.

*Reproductive organs*.—Androecium: Not observed. Gynoecium: Number of pistils per ray floret: One. Pistil length: About 4 mm. Style length: About 3.8 mm. Style color: Close to 151B. Stigma diameter: About 0.5 mm. Stigma shape: Forked. Stigma color: Close to 151B.

*Seeds and fruits*.—To date seed and fruit production have not been observed on plants of the new *Chrysanthemum*.

Garden performance: Plants of the new *Chrysanthemum* have demonstrated good garden performance and will tolerate temperatures ranging from about 4° C. to about 30° C.

It is claimed:

1. A new and distinct *Chrysanthemum* plant named 'Zanmumamia' as illustrated and described.

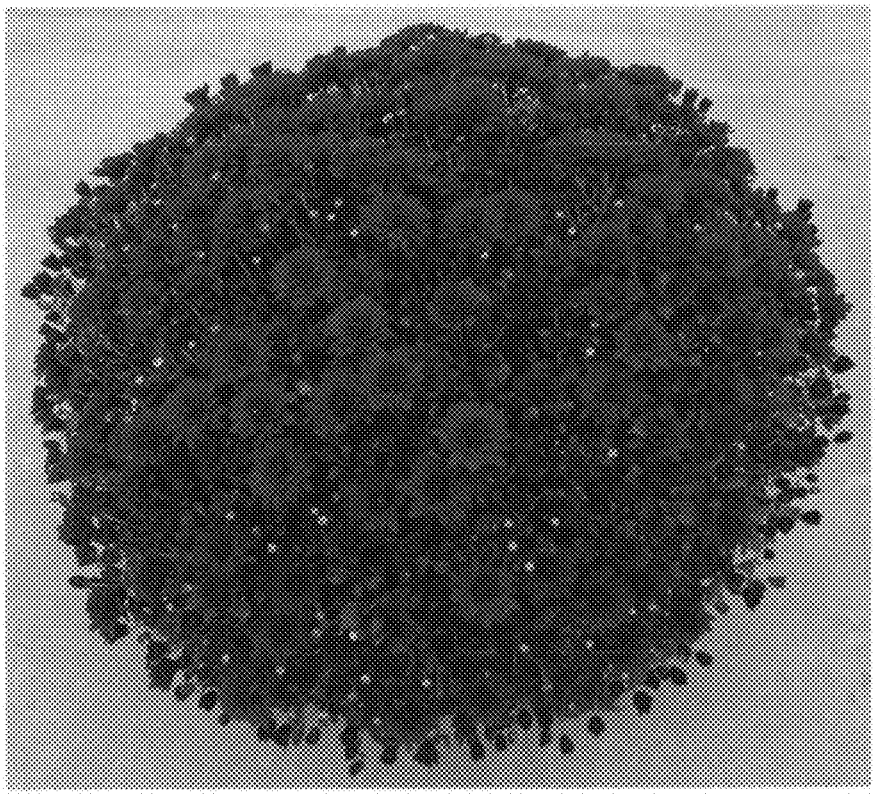

* * * * *